United States Patent [19]

Sano et al.

[11] 4,303,630

[45] Dec. 1, 1981

[54] PROCESS FOR THE PRODUCTION OF CARBON MONOXIDE

[75] Inventors: Kozo Sano; Hideo Igarashi; Takeo Ikarashi, all of Niigata, Japan

[73] Assignee: Mitsubishi Gas Chemical Company, Inc., Tokyo, Japan

[21] Appl. No.: 175,839

[22] Filed: Aug. 6, 1980

[30] Foreign Application Priority Data

Aug. 17, 1979 [JP] Japan .................................. 54-104621
Mar. 3, 1980 [JP] Japan .................................. 55-26366

[51] Int. Cl.³ ...................... C01B 31/18; C07C 31/04
[52] U.S. Cl. .................................. 423/415 A; 568/876
[58] Field of Search ..................... 423/415 A; 568/876

[56] References Cited

U.S. PATENT DOCUMENTS

| 3,716,619 | 2/1973 | Lynn et al. | 423/247 |
| 3,812,210 | 5/1974 | Higdon et al. | 423/415 A X |
| 4,232,170 | 11/1980 | Grey et al. | 423/415 A X |

FOREIGN PATENT DOCUMENTS 52-36609 3/1977 Japan .................................. 568/876

*Primary Examiner*—Earl C. Thomas
*Attorney, Agent, or Firm*—Koda and Androlia

[57] ABSTRACT

Carbon monoxide of high purity and methanol can be obtained from a mixture of methyl formate and methanol without eliminating methanol or isolating methyl formate from the mixture by selectively pyrolyzing methyl formate alone in the presence of an alkali metal compound other than alkali metal alcoholates.

12 Claims, No Drawings

PROCESS FOR THE PRODUCTION OF CARBON MONOXIDE

BACKGROUND OF THE INVENTION

1. Field of the Invention

The present invention relates to a process for the production of carbon monoxide of high purity by pyrolyzing of methyl formate. More particularly, the present invention relates to a process for the production of carbon monoxide wherein methyl formate alone in a mixture of methyl formate and methanol is selectively subjected to catalytic pyrolysis to obtain carbon monoxide of high purity and methanol.

2. Description of the Prior Arts

Usually known as a process for producing methyl formate are a process wherein methanol is reacted with carbon monoxide ($CH_3OH + CO \rightarrow HCOOCH_3$), a process wherein formic acid is esterified with methanol ($HCOOH + CH_3OH \rightarrow HCOOCH_3 + H_2O$) and a process wherein methanol is subjected to dehydrogenation reaction ($2CH_3OH \rightarrow HCOOCH_3 + 2H_2$). In these reactions, the conversion of methanol is not so high that the resultant reaction mixture substantially is a mixture of unreacted methanol and the produced methyl formate. If methyl formate alone in such mixture of methyl formate and methanol is selectively decomposed to carbon monoxide and methanol, it will be of very industrial significance in that carbon monoxide of high purity can directly be obtained from the mixture of methyl formate and methanol without eliminating methanol from the reaction mixture in the synthesis of methyl formate or without isolating methyl formate from the reaction mixture.

On the other hand, known prior art processes of the pyrolysis of methyl formate involve (i) a process wherein methyl formate is subjected to pyrolysize in vapor phase conducted at 200°-500° C. in the presence of a solid catalyst comprising an alkaline earth metal oxide such as barium oxide or calcium oxide (U.S. Pat. No. 3,812,210), (ii) a process wherein methyl formate is pyrolyzed at a temperature of 200°-550° C. by the aid of active carbon as catalyst (Japanese Laid-Open Patent Appln. No. 36609/77) and (iii) a process wherein methyl formate in the co-existence of methanol is pyrolyzed under a pressure of at most 250 psig (175 kg/cm$^2$) and at a temperature of 35°-200° C., using a catalyst sodium methylate which has been used for the synthesis of methyl formate from methanol and carbon monoxide (U.S. Pat. No. 3,716,619).

Among the above mentioned three processes, however, the processes (i) and (ii) are effective only in case of using pure methyl formate free from methanol as starting material and show a slow reaction velocity when applied to methyl formate in a mixture of methanol and methyl formate utilized for the present invention. Further, in case of applying the process (ii), a large amount of hydrogen is included in the evolved gas, thus making it impossible to obtain carbon monoxide of high purity. In the process (iii) sodium methylate used as catalyst is reacted within the adopted temperature range of 35°-200° C. with methyl formate and easily converted into other compounds so that methyl formate is wasted to reduce selectivity of methyl formate to carbon monoxide, and at the same time, dimethyl ether evolved in this reaction contaminates carbon monoxide. In the above mentioned processes (i)-(iii), methyl formate alone in a mixture of methyl formate and methanol could not selectively be pyrolyzed at such a space velocity as adopted in the present invention and as a result carbon monoxide of high purity could not be obtained.

SUMMMARY OF THE INVENTION

It is an object of the present invention to provide a process for the production of carbon monoxide wherein carbon monoxide of high purity and methanol can be obtained in a simple step from a mixture of methyl formate and methanol without eliminating methanol or isolating methyl formate therefrom.

It is another object of the present invention to provide a process for the production of carbon monoxide wherein the decomposition rate of methyl formate, the selectivity to carbon monoxide and methanol are high and carbon monoxide of high purity can be obtained without the formation of any by-product.

It is still another object of the present invention to provide a process for the production of carbon monoxide wherein the amount of the catalyst used is small and deterioration of the catalytic activity is extremely low so that carbon monoxide of high purity can be obtained.

The present inventors have made extensive researches for developing a process for the production of carbon monoxide of high purity wherein methyl formate alone in a mixture of methyl formate and methanol is selectively subjected to catalytic pyrolysis. As a result of such researches, it has now been found that an alkali metal compound which has no or little reactivity with methanol or methyl formate is an extremely effective catalyst for such pyrolysis. The present invention has been accomplished on the basis of the above finding.

In accordance with the present invention, there is provided a process for the production of carbon monoxide characterized in that methyl formate alone in a mixture of methyl formate and methanol is selectively pyrolyzed in the presence of an alkali metal compound other than alkali metal alcoholates to obtain carbon monoxide of high purity and methanol.

DETAILED DESCRIPTION OF THE INVENTION

A mixture of methyl formate and methanol used in the present invention (referred to hereinafter as the starting mixture) may be one obtained by any of the reactions. For example, the reaction products in the insertion reaction of carbon monoxide to molecular methanol wherein a gas containing carbon monoxide and hydrogen such as coal gas is used, the esterification reaction of formic acid with methanol and the dehydrogenation reaction of methanol. These reaction products are freed from catalysts and can directly be used as the starting material for producing carbon monoxide in the present invention without necessity of separating methyl formate and methanol from the reaction products.

Especially preferable is the case of the starting mixture prepared by dehydrogenation of methanol for the production of carbon monoxide according to the pyrolysis of the present invention because hydrogen and carbon monoxide are produced separately as having a high purity from methanol, and methanol by-produced in the pyrolysis of methyl formate may be returned and reused as the raw material in the process for producing methyl formate with dehydrogenation of methanol.

No particular limitation exists in the concentration of methyl formate in the starting mixture, but the concentration is practically limited usually to 10-70 wt. %, preferably 20-60 wt. %. If the concentration is less than 10 wt. %, the yield of carbon monoxide based on the starting mixture will be decreased. On the other hand, if the concentration is higher than 70 wt. %, the amount of hydrogen evolved will be larger to decrease the purity of carbon monoxide. However, such reasons do not disturb the use of a mixture having a methyl formate concentration of lower than 10 wt. % or higher than 70 wt. % as the starting mixture.

The catalyst utilizable in the present invention is an alkali metal compound other than alkali metal alcoholates, which has no or little reactivity with methanol or methyl formate. Illustrative of the catalyst are, for example, hydroxides, sulfides, halides, sulfates, carbonates and the like inorganic acid salts of alkali metals such as potassium, sodium, lithium and cesium as well as organic acid salts such as formates and acetates of these alkali metals. Examples of the typical compounds include potassium hydroxide, potassium chloride, potassium formate, sodium sulfide, sodium sulfate, sodium carbonate and lithium chloride. These alkali metal compounds can be used singly or as a mixture or in the form supported on a carrier.

Preferable carriers are neutral or basic substances such as diatomaceous earth, brick, pumice, silica gel and active carbon.

No particular limitation exists in the amount of the catalyst supported on these carriers but the amount is practically limited in such manner that the catalyst is present in an amount of 0.05-3 milliatoms, preferably 0.1-1.5 milliatoms in terms of alkali metal atom per gram of the carrier.

The catalyst is utilized in such form that the alkali metal compound itself is dissolved homogeneously in the starting mixture or slurried therewith, if the compound is sparingly soluble in the starting mixture. Then the alkali metal compound fed into a reactor where the reaction is carried out batchwise or continuously. In case of the continuous reaction, a fixed bed continuous method can be adopted wherein the alkali metal compound itself or a catalyst comprising the alkali metal compound supported on the carrier is previously charged into a reactor and the starting mixture is continuously supplied to the reactor while discharging the reaction product continuously therefrom. A fluidized bed or moving bed can also be utilized for the continuous reaction. Among these methods for continuous reaction, preferable is the method with a fixed bed. The amount of the catalyst varies with a method used catalyst. In case of the fixed bed continuous method, no particular limitation exists in the amount of the catalyst. In case of the reaction operation comprising supplying the catalyst in mixture with the starting mixture to the reactor or supplying the catalyst separately with the starting mixture to the reactor is carried out batchwise or continuously, the amount of the catalyst is practically limited in such manner that the catalyst is present in an amount of 0.1-400 milliatoms, preferably 0.4-100 milliatoms in terms of alkali metal atom per mol of methyl formate. If the amount of the catalyst used is less than 0.1 milliatom in terms of alkali metal atom per mol of methyl formate, the reaction velocity will become slower. On the other hand, if the amount exceeds 400 milliatoms, there may be danger of any side decomposition reaction of methanol or methyl formate.

The reaction temperature may be within the temperature range of pyrolyzing methyl formate in conventional methods, but is practically within the temperature range of 200°-500° C., preferably 250°-450° C. The pyrolyzing reaction velocity of methyl formate is not satisfactory at a reaction temperature lower than 200° C., while the amount of methyl formate consumed by side reactions increase at a reaction temperature above 500° C. so that the yield of carbon monoxide is decreased and at the same time decomposition of methanol also takes place to contaminate the carbon monoxide evolved.

No particular limitation exists in the reaction pressure; a satisfactory reaction velocity is maintained and carbon monoxide of high purity is produced not only under atmospheric pressure but also under superatmospheric pressure as high as 350 atm. under which the reaction velocity was considered to be slow from the past. According to the process of the present invention for producing carbon monoxide, therefore, carbon monoxide of high purity maintained at any desired pressure can be obtained without necessity of any special compression. In the present invention the reaction is carried out in vapor phase or liquid phase but the reaction in vapor phase is preferable from the practical point of view. By carrying out the reaction in such manner as above mentioned, the period of reaction time can be shortened or prolonged in the present invention so that the reaction time for a batch process is within the period from 30 seconds to 4 hours, especially 0.1-2 hours, while that for a continuous reaction is within the extent of 1-100, preferably 2-50 in terms of liquid space velocity per hour (referred to hereinafter simply as LSVH) or within the extent of 500-50,000, preferably 1,000-25,000 (at NTP) in terms of gas space velocity per hour (referred to hereinafter simply as GSVH).

The gas itself obtained in the present invention contains carbon monoxide of satisfactorily high purity. If necessary, the gas may be used after washing with water or alkaline water. Methanol obtained concurrently can be used as such or after purification as a starting material for preparing methyl formate.

In the present invention, simplification of the steps is possible since a mixture of methyl formate and methanol is subjected directly, without eliminating methanol or isolating methyl formate from the mixture, to catalytic pyrolysis whereby methyl formate alone in the mixture is pyrolyzed. Further, the decomposition rate of methyl formate and selectivity to carbon monoxide and methanol are high respectively and the catalyst stable against deterioration does not permit the formation by by-products, thus making it possible to obtain carbon monoxide of high purity. Furthermore, the amount of the catalyst used is small and the catalyst is resistant to deterioration of catalytic activity and is tolerant to the use for an extremely prolonged period of time. Thus, the present invention is significantly high in industrial value.

The following examples are given only for illustration of the present invention but are not construed to limit the invention to the embodiments illustrated. In examples and comparative examples, the yields of methanol and carbon monoxide are based on methyl formate.

EXAMPLES 1-11

An autoclave having a capacity of 100 ml was charged with given amounts of the catalyst and the starting mixture of methyl formate and methanol. The mixture was stirred at a given reaction temperature for a given period of reaction time to effect a batch reaction. After the reaction, the autoclave was cooled and the gas evolved was released therefrom. The released gas and the liquid discharged from the autoclave were respectively analyzed to determine their compositions. The pressure, conversion of methyl formate, yields of carbon monoxide, yields of methanol and the compositions of the evolved gases at the time of completion of the reaction were as shown in Table I-1 and Table I-2.

COMPARATIVE EXAMPLE 1

The reaction was carried out under the same condition as described in Example 1 except that calcium oxide was used in place of potassium hydroxide. A result of the reaction was as shown in Table I-2.

As are evident from Table I-2, the conversion of methyl formate, the yield of methanol and the yield of carbon monoxide were all very poor as compared with the cases of Example 1.

COMPARATIVE EXAMPLE 2

The reaction was carried out under the same condition as described in Example 10 except that sodium methylate was used in place of potassium chloride. A result of the reaction was as shown in Table I-2.

As are evident from Table I-2, the purity of carbon monoxide was low and the conversion rate of methyl formate an the yields of methanol and the yields of carbon monoxide were very poor as compared with the cases of Example 10.

EXAMPLES 12-16

A reaction tube was charged with a solid catalyst and the reaction was carried out continuously by continuously supplying the starting mixture thereto at a given temperature and a given GSVH (LSVH) under a given pressure. The reaction product continuously discharged was cooled and the gas evolved and the liquid were analyzed to determine their compositions. Table II shows the conversion rate of methyl formate, the yield of carbon monoxide, the yield of methanol calculated from the result of analysis and the composition of the evolved gas.

COMPARATIVE EXAMPLE 3

The pyrolysis reaction of the starting mixture was carried out continuously under the substantially same conditions as described in Example 16 except that the reaction tube was charged with active carbon. A result of the reaction was as shown in Table II.

As shown in Table II, the content of hydrogen in the evolved gas was high but the content of carbon monoxide in the gas and the yield of methanol were low as compared with the cases of Example 15.

EXAMPLE 17

A stainless steel reactor was charged with 5.9 cc of a catalyst comprising sodium hydroxide supported on diatomaceous earth and containing the sodium hydroxide in an amount of 1.25 milliatoms in terms of sodium metal per gram of the carrier. The starting mixture consisting of 29.7 wt. % of methyl formate and 70.3 wt. % of methanol was continuously fed into the reactor under conditions involving a reaction temperature of 310° C. and a reaction pressure of 10 kg/cm$^2$G so that GSVH in the reactor might be maintained at 30,000 hr$^{-1}$, while continuously discharging the reaction product in an amount almost equal to that of the starting mixture. The gas evolved had the following composition: 98.8 vol. % carbon monoxide, 0.6 vol. % hydrogen, 0.2 vol. % methane and 0.4 vol. % carbon dioxide. The conversion of methyl formate was 98.8% and the yields of carbon monoxide and the yields of methanol were 98.0% and 97.8%, respectively.

EXAMPLES 18-20

The reactions were carried out by feeding the starting mixtures of various compositions into the reactor charged with the solid catalyst under conditions involving given temperatures, given pressures are given GSVH in the same manner as described in Example 17.

Table III shows the reaction conditions and a result of the reactions.

TABLE I-1

| | Example 1 | 2 | 3 | 4 | 5 | 6 |
|---|---|---|---|---|---|---|
| Starting mixture | | | | | | |
| Methyl formate (g) | 11.60 | 10.28 | 10.50 | 10.75 | 10.35 | 9.67 |
| Methanol (g) | 21.29 | 20.32 | 22.03 | 21.90 | 20.08 | 21.33 |
| Catalyst | | | | | | |
| Sort | potassium hydroxide | potassium chloride | sodium sulfide | sodium sulfate (anhydrous) | sodium carbonate (anhydrous) | sodium formate |
| Amount used (mg) | 51.7 | 50.7 | 63.4 | 32.8 | 74.0 | 41.9 |
| milliatom/methyl formate (mol) | 4.8 | 3.9 | 9.3 | 2.6 | 8.1 | 3.8 |
| Temperature (°C.) | 300 | 300 | 300 | 300 | 300 | 300 |
| Reaction time (hr) | 1.0 | 0.15 | 1.0 | 1.0 | 0.15 | 1.0 |
| Pressure (kg/cm$^2$G) | 285 | 250 | 245 | 247 | 250 | 270 |
| Conversion of methyl formate (%) | 88.9 | 91.3 | 87.4 | 85.3 | 86.8 | 86.7 |
| Yield of carbon monoxide (%) | 85.0 | 88.0 | 82.8 | 83.2 | 79.5 | 81.5 |
| Yield of methanol (%) | 86.6 | 86.5 | 83.1 | 82.5 | 77.8 | 80.9 |
| Composition of gas evolved (vol %) | | | | | | |
| Carbon monoxide | 94.3 | 95.7 | 94.1 | 92.8 | 93.7 | 96.7 |
| Carbon dioxide | 2.7 | 1.7 | 2.1 | 2.2 | 2.4 | 1.1 |
| Methane | 0.1 | 0.1 | 0.1 | 0.3 | 0.1 | 0.1 |
| Hydrogen | 2.9 | 2.5 | 3.7 | 4.7 | 3.8 | 2.1 |

TABLE I-1-continued

|  | Example 1 | 2 | 3 | 4 | 5 | 6 |
|---|---|---|---|---|---|---|
| Others | 0 | 0 | 0 | 0 | 0 | 0 |

TABLE I-2

|  | Example 7 | 8 | 9 | 10 | 11 | Comparative Example 1 | 2 |
|---|---|---|---|---|---|---|---|
| Starting mixture | | | | | | | |
| Methyl formate (g) | 18.02 | 15.01 | 10.52 | 10.24 | 8.79 | 11.50 | 10.28 |
| Methanol (g) | 12.01 | 15.34 | 21.35 | 21.85 | 16.73 | 21.32 | 21.48 |
| Catalyst | | | | | | | |
| Sort | potassium hydroxide | potassium chloride | lithium chloride | potassium chloride | potassium chloride | calcium oxide | sodium methylate |
| Amount used (mg) | 47.5 | 49.5 | 35.1 | 700.4 | 11.2 | 49.4 | 508.4 |
| milliatom/methyl formate (mol) | 2.8 | 2.7 | 4.7 | 54.9 | 1.0 | 4.6 | 55.0 |
| Temperature (°C.) | 320 | 250 | 290 | 300 | 400 | 300 | 300 |
| Reaction hour (hr) | 1.0 | 1.0 | 1.0 | 1.5 | 2.0 | 1.0 | 1.0 |
| Pressure (kg/cm$^2$G) | 350 | 293 | 290 | 263 | 275 | 173 | 260 |
| Conversion of methyl formate (%) | 85.7 | 86.4 | 84.9 | 85.1 | 93.5 | 10.2 | 73.5 |
| Yield of carbon monoxide (%) | 84.1 | 83.9 | 81.8 | 80.1 | 88.5 | 3.6 | 70.7 |
| Yield of methanol (%) | 83.9 | 83.1 | 81.3 | 79.8 | 87.1 | 1.1 | 65.1 |
| Composition of gas evolved (vol %) | | | | | | | |
| Carbon monoxide | 93.8 | 95.2 | 94.8 | 95.4 | 95.1 | 93.3 | 91.7 |
| Carbon dioxide | 2.9 | 2.1 | 2.3 | 1.9 | 2.2 | 4.9 | 0.6 |
| Methane | 0.1 | 0.1 | 0.1 | 0.1 | 0.1 | 0.1 | 0 |
| Hydrogen | 3.2 | 2.6 | 2.8 | 2.6 | 2.6 | 1.7 | 0.9 |
| Others | 0 | 0 | 0 | 0 | 0 | 0 | *6.8 |

*Dimethyl ether

TABLE II

|  | Example 12 | 13 | 14 | 15 | 16 | Comparative Example 3 |
|---|---|---|---|---|---|---|
| Starting mixture | | | | | | |
| Methyl formate (g/hr) | 126.2 | 96.5 | 51.2 | 184.9 | 126.5 | 125.9 |
| Methanol (g/hr) | 308.2 | 235.8 | 122.0 | 452.6 | 308.3 | 308.1 |
| Solid catalyst | | | | | | |
| Carrier | active carbon | brick | — | active carbon | active carbon | active carbon |
| Supported alkali metal | potassium chloride | sodium carbonate (anhydrous) | potassium chloride | potassium chloride | potassium chloride | — |
| Amount supported (metal in terms of milliatoms per gram of carrier) | 0.27 | 0.19 | — | 0.54 | 0.27 | — |
| Temperature (°C.) | 300 | 300 | 330 | 270 | 300 | 300 |
| Reaction time GSVH | 2630 | 2000 | 1030 | 3850 | 2620 | 2620 |
| (corresponding LSVH) | (5.1) | (3.9) | (2.0) | (7.5) | (5.1) | (5.1) |
| Pressure (kg/cm$^2$G) | 100 | 10 | 30 | 0 | 10 | 10 |
| Conversion of methyl formate (%) | 98.5 | 98.3 | 99.4 | 99.8 | 99.5 | 97.4 |
| Yield of carbon monoxide (%) | 98.2 | 97.6 | 99.2 | 99.5 | 99.1 | 95.3 |
| Yield of methanol (%) | 95.8 | 96.1 | 98.9 | 96.2 | 99.3 | 80.6 |
| Composition of gas evolved (vol %) | | | | | | |
| Carbon monoxide | 99.5 | 98.3 | 98.0 | 98.1 | 98.0 | 82.1 |
| Carbon dioxide | 0.1 | 0.5 | 1.3 | 1.1 | 0.7 | 1.1 |
| Methane | 0.1 | 0.1 | 0.2 | 0.1 | 0.1 | 0.5 |
| Hydrogen | 0.3 | 1.1 | 0.5 | 0.7 | 1.2 | 16.3 |
| Others | 0 | 0 | 0 | 0 | 0 | 0 |

TABLE III

| | Example 18 | 19 | 20 |
|---|---|---|---|
| Composition of the starting mixture | | | |
| Methyl formate (wt. %) | 43.3 | 35.0 | 51.5 |
| Methanol (wt. %) | 56.7 | 65.0 | 48.5 |
| Solid catalyst | | | |
| Carrier | brick | active carbon | active carbon |
| Supported alkali metal compounds | potassium hydroxide | potassium chloride | potassium hydroxide + sodium hydroxide |
| Amount supported (metal in terms of milliatom per gram of carrier) | 0.54 | 0.27 | 1.53 |
| Reaction conditions | | | |
| Temperature (°C.) | 320 | 308 | 350 |
| GSVH | 7500 | 15000 | 6000 |
| Pressure (kg/cm$^2$G) | 150 | 50 | 300 |
| Conversion of methyl formate (%) | 98.0 | 98.5 | 94.8 |
| Yield of carbon monoxide (%) | 97.1 | 97.4 | 92.9 |
| Yield of methanol (%) | 96.1 | 96.9 | 91.5 |
| Composition of gas evolved (vol %) | | | |
| Carbon monoxide | 98.2 | 98.7 | 98.0 |
| Hydrogen | 1.1 | 0.6 | 1.4 |
| Methane | 0.3 | 0.2 | 0.3 |
| Carbon dioxide | 0.4 | 0.5 | 0.3 |

What is claimed is:

1. A process for the production of carbon monoxide, characterized by selectively pyrolyzing methyl formate alone in a mixture of methyl formate and methanol in a temperature range wherein said methyl formate pyrolyzes in presence of an alkali metal compound which as substantially no reactivity with methanol and methyl formate and which is other than alkali metal alcoholates to obtain carbon monoxide of high purity and methanol.

2. A process according to claim 1 wherein said mixture of methyl formate and methanol contains 10–70 wt. % methyl formate.

3. A process according to claim 1 wherein said alkali metal compound is a compound of an alkali metal selected from the group consisting of potassium, sodium, lithium and cesium.

4. A process according to claim 1 wherein the reaction operation comprising supplying said alkali metal compound in mixture with said starting mixture to the reactor or supplying said alkali metal compound separately with said starting mixture to the reactor is carried out batchwise or continuously.

5. A process according to claim 4 wherein said alkali metal compound is used in an amount of 0.1–400 milliatoms in terms of alkali metal per mol of methyl formate.

6. A process according to claim 1 wherein said alkali metal compound is used in such solid catalyst form that said alkali metal compound itself is supported on a carrier.

7. A process according to claim 6 wherein said solid catalyst is supported on a neutral to basic carrier.

8. A process according to claim 6 wherein said solid catalyst is used in a fixed bed charged in the reactor.

9. A process according to claim 6 wherein said solid catalyst comprises said alkali metal compound supported on said carrier, the amount of said alkali metal compound being 0.05–3.0 milliatom in terms of alkali metal atom per gram of said carrier.

10. A process according to claim 1 wherein said alkali metal compound is one or mixture thereof selected from the group consisting of hydroxide, sulfide, inorganic acid salts of alkali metal and organic acid salts of said alkali metals.

11. A process according to claim 1 wherein a reaction temperature is 200°–500° C.

12. A process according to claim 10, wherein said alkali metal is selected from the group consisting of potassium, sodium, lithium and cesium.

* * * * *